United States Patent
Ihamäki et al.

(10) Patent No.: US 7,308,295 B2
(45) Date of Patent: *Dec. 11, 2007

(54) COMPILATION OF IMAGE INFORMATION AND MAMMOGRAPHY APPARATUS FOR PERFORMING BIOPSY

(75) Inventors: Timo Ihamäki, Vantaa (FI); Petri Jouhikainen, Järvenpää (FI)

(73) Assignee: Instrumentarium Corporation (FI)

( * ) Notice: Subject to any disclaimer, the term of this patent is extended or adjusted under 35 U.S.C. 154(b) by 580 days.

This patent is subject to a terminal disclaimer.

(21) Appl. No.: 10/123,612

(22) Filed: Apr. 16, 2002

(65) Prior Publication Data

US 2002/0156360 A1    Oct. 24, 2002

(30) Foreign Application Priority Data

Apr. 20, 2001    (FI) .................................. 20010810

(51) Int. Cl.
*A61B 5/00* (2006.01)
(52) U.S. Cl. ..................... 600/407; 600/425; 600/427; 600/439; 378/37; 378/39; 378/108; 378/147; 606/130
(58) Field of Classification Search ................ 600/407, 600/425, 427, 429, 439; 606/130; 378/37, 378/39, 108, 147, 208; 128/920
See application file for complete search history.

(56) References Cited

U.S. PATENT DOCUMENTS

| | | | |
|---|---|---|---|
| 4,324,978 A | * | 4/1982 | Kalender et al. ............... 378/4 |
| 4,817,125 A | | 3/1989 | Sklebitz |
| 5,107,843 A | | 4/1992 | Aarnio et al. |
| 5,219,351 A | | 6/1993 | Teubner et al. |
| 5,409,497 A | * | 4/1995 | Siczek et al. ............... 600/407 |
| 5,594,769 A | * | 1/1997 | Pellegrino et al. ............ 378/37 |
| 5,872,828 A | | 2/1999 | Niklason et al. |
| 6,081,577 A | | 6/2000 | Webber |
| 6,208,710 B1 | | 3/2001 | Nagai |

FOREIGN PATENT DOCUMENTS

EP    1008325    6/2000

* cited by examiner

*Primary Examiner*—Brian L. Casler
(74) *Attorney, Agent, or Firm*—Andrus, Sceales, Starke & Sawall, LLP

(57) ABSTRACT

A mammography apparatus has a bracket having one of its arms fitted with an X-ray tube head. The X-ray tube head is formed of an X-ray tube for producing X-radiation and a collimator for collimating the X-radiation. The bracket arm opposite the X-ray tube head is fitted with an image forming element. The bracket is further provided with a compression means for compressing a breast during an imaging procedure. The image forming element has a digital full field detector. The mammography apparatus has integrable therewith a biopsy device with a biopsy needle. The detector required in a biopsy imaging process for imaging the volume space of biopsy is formed of a desired element of the full field detector. A needle guiding unit is provided for a guided movement of the biopsy needle in the volume space of biopsy on the basis of three-dimensional information compiled in the biopsy imaging process.

9 Claims, 4 Drawing Sheets

COMPILATION OF IMAGE INFORMATION AND MAMMOGRAPHY APPARATUS FOR PERFORMING BIOPSY

CROSS REFERENCE TO RELATED APPLICATION

The present application claims priority from Finnish Patent Application No. 20010810, filed Apr. 20, 2001.

SUMMARY OF THE INVENTION

For example, western lifestyles (greasy diet etc.) have attributed to the fact that occurrence of breast cancer in women is more and more widespread. In the United States alone, approximately 180,000 new cases of breast cancer was detected in 2000 and approximately 41,000 patients were lost because of breast cancer. Since the question is about a high-risk illness, much attention is paid in more and more countries for sufficiently early detection of breast cancer. Such control is effected by means of mammography equipment.

In Finland, for example, every woman has a possibility of having her breasts examined. In the first phase of breast examination, the entire breast is imaged by using either a film of sufficiently large surface area or a full field detector having a surface area which is for example 18 cm*24 cm. Women in a particular age group are subjected to a free-of-charge screening examination, wherein each breast is exposed to a mammography apparatus for two images from different directions. Should anything suspicious be observed in the screening test, the investigation will be followed by clinical examination. In clinical examination, the part of a breast fallen under suspicion is either subjected to additional images from various directions or the suspicious part of a breast is subjected to biopsy. Another way of taking additional images is to compress or squeeze the breast over the area in which a doubtful object is located, followed by taking an enlarged image of the object. This is a way of achieving extra confirmation of an object, and if the object is still found suspicious, a biopsy procedure is performed. In biopsy, a biopsy needle is used to pick up a number of cells sufficient for a reliable analysis of the examined tissue.

In prior art, biopsy is performed by applying manual biopsy or biopsy based on stereotactic imaging. Manual biopsy involves taking two images at 90-degree angles, on the basis of which images a physician picks up a sample from a suspicious part of the breast. A drawback in manual biopsy is inaccuracy with regard to biopsy, which in a worst scenario may lead to an incorrect negative diagnosis. Biopsy based on stereotactic imaging involves taking an image of a suspicious part of the breast from two different angles. In the past, imaging was performed on film, but nowadays more and more often with a digital detector, such as for example with a 5 cm*5 cm sized CCD (Charge Coupled Device) detector. Such images are used for calculating xyz-coordinates comprising three-dimensional information, on the basis of which a biopsy needle can be guided to a desired part of the breast for biopsy. A drawback in this prior art is a separate arrangement for biopsy, said arrangement comprising a film or a digital detector. All prior known digital biopsy devices have used small-area detectors, such as for example 5 cm*5 cm surface area detectors. Said detector must be placed in position very carefully in order to perform biopsy from a suspicious section of the breast.

BRIEF DESCRIPTION OF THE INVENTION

The present invention relates to a mammography apparatus, comprising a bracket having one of its arms fitted with an X-ray tube head and its opposite arm with an image forming element, the latter comprising a full field detector. The bracket is further provided with compression means for compressing the breast during imaging. For example, said compression means may comprise two compression plates between which breast is compressed or a compression plate by which the breast is compressed against the image forming element. The invention relates also to a method for performing biopsy.

The X-ray imaging apparatus used for X-ray mammographic examination is generally similar to what is shown in FIG. 1, comprising a C-shaped bracket 1, 5, 6, having its opposite arms 1, 6 fitted with an X-ray tube head 12 and an image forming element 23, the latter comprising a full field detector 11. The bracket is further provided with a movable compression plate 7 for compressing the breast against the image forming element 23. The bracket is bearing-mounted pivotably about a journal 8 set in parallel with the arms 1, 6 and secured substantially perpendicularly to a connecting bar 5 linking the same together. The journal 8, on the other hand, is secured to a slide block 9 movable along an upright 10 in view of providing a vertical adjustment for the apparatus.

It is an object of the invention to provide an improved solution for performing biopsy in relation to mammography imaging procedures. According to the invention, this is achieved by means of a mammography apparatus, comprising a bracket having one of its arms fitted with an X-ray tube head, comprising an X-ray tube for producing X-radiation and a collimator for collimating X-radiation, and the bracket arm opposite to the X-ray tube head is fitted with an image forming element, said image forming element comprising a digital full field detector, and said bracket being further provided with compression means for compressing the breast during imaging, said mammography apparatus being characterized in that the mammography apparatus also has integrable therewith is a biopsy device, comprising a biopsy needle, and that the mammography apparatus further comprises, as a detector required in a biopsy imaging process, a desired element of said full field detector for imaging the volume space of biopsy and a needle guiding unit for a guided movement of the biopsy needle in said volume space of biopsy on the basis of three-dimensional information compiled in said biopsy imaging. In a method of the invention for performing biopsy from a breast, the breast is compressed for holding the same for the duration of a biopsy procedure in an essentially static position in the mammography apparatus. The biopsy device is integrated with the mammography apparatus in such a way that the biopsy imaging required in biopsy is performed from a suspicious part of the breast by using, as an imaging detector, a desired element of a full field detector included in the mammography apparatus, and a biopsy needle included in the biopsy device is guided to pick up a test specimen from a suspicious part of the breast on the basis of three-dimensional information compiled in said biopsy imaging.

Another object of the invention is to minimize X-radiation applied to a patient. This is accomplished by means of an arrangement of the invention for compiling image information, said arrangement comprising a detector. The arrangement comprises elements for localizing an object from compiled image information, a collimator for performing the collimation of radiation applied to the localized object, and imaging instruments for performing collimated imaging by using such a section of the detector imaging field which images said collimated exposure area. The invention relates also to a method for compiling image information, said method comprising compiling image information about a relevant object. The method involves the localization of an object from compiled image information, the collimation of radiation applied to the localized object, and the performance of collimated imaging by using for the imaging such a section of the detector imaging field which images said collimated exposure area.

The invention is based on the fact that a biopsy device is integrable with a mammography apparatus in such a way that biopsy imaging can be effected by means of a common full field detector, which is used for imaging procedures of the entire breast. The biopsy needle is guided for movement within a three dimensional volume space required for biopsy.

The invention is also based on the fact that image information is compiled from an examined volume space by means of a detector, followed by localizing an object from the compiled image information, the image field required for imaging the object being collimated such that imaging of the object is effected by using just a necessary element of the detector.

An advantage gained by the inventive solution is that one and the same detector configuration can be used both for full-scale breast imaging procedures and for biopsy, which focuses on a volume space smaller than the entire breast. The inventive solution is a practical implementation which requires no time for the installation of various detectors in various examination conditions. Another major benefit gained by the invention is the minimization of the amount of X-radiation applied to a patient due to the fact that X-radiation is only applied or focused on a volume space as small as possible.

The invention will now be described in more detail with reference to the accompanying drawings, in which:

DETAILED DESCRIPTION OF THE INVENTION

Figure 1:
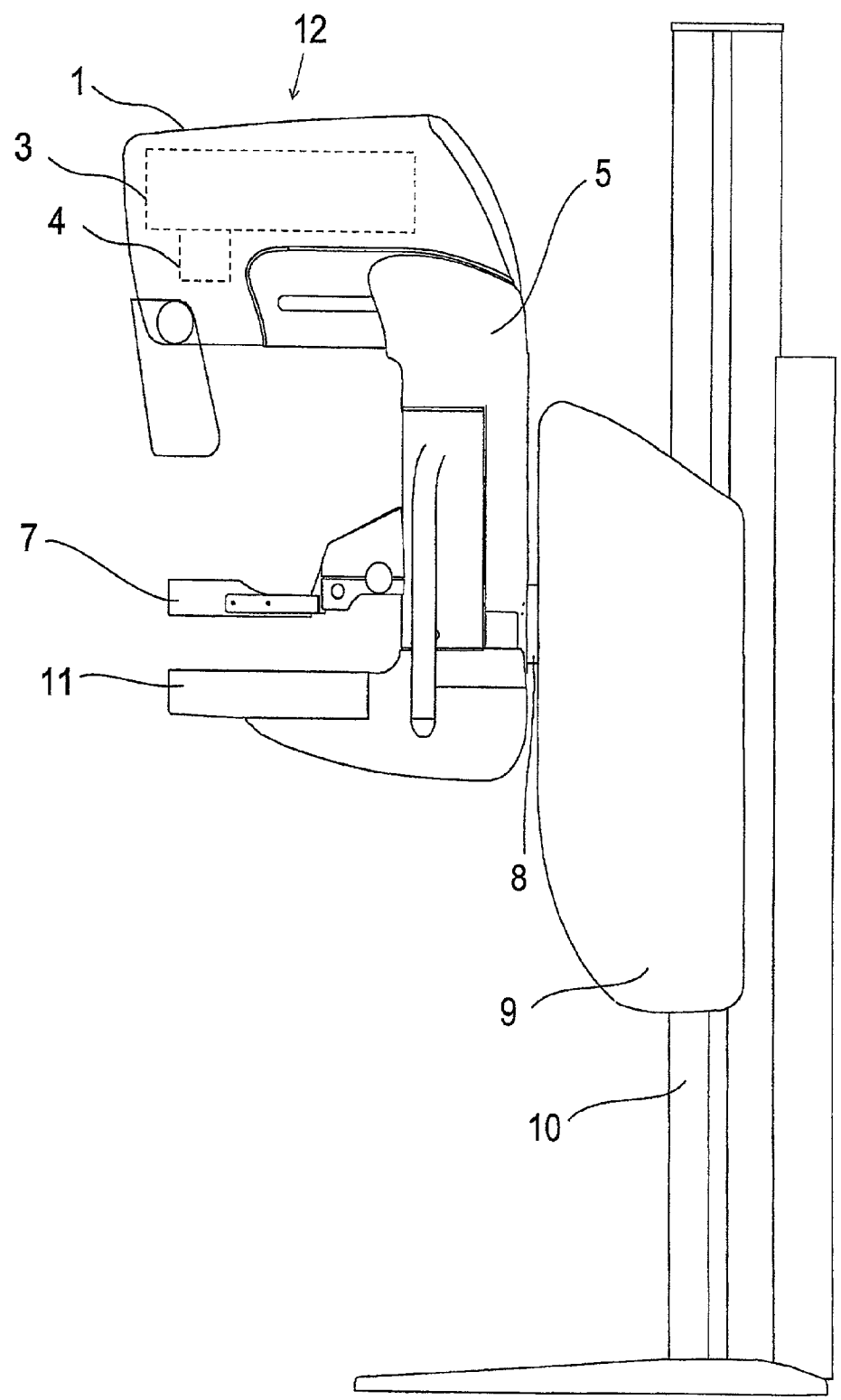
FIG. 1 shows schematically an X-ray imaging apparatus of the prior art used for mammography.

In the first phase of breast examination, an image is taken of the entire breast. The equipment used for this comprises nowadays more and more digital mammography devices, wherein X-rays emitted through the breast are received by a digital full field detector. One example of a digital mammography apparatus is depicted in FIG. 1, which has already been discussed above. The surface area of a full field detector is usually sufficient for imaging the entire breast in a single imaging procedure. The surface area of a full field detector is for example 18 cm×24 cm. The X-ray image of the entire breast is examined for example at a computer screen. A suspicious part detected from the X-ray image is localized for biopsy. In biopsy, a test specimen is taken from a suspicious part of the breast, said test specimen being used as a basis to find out what type of tissue is present in the suspicious part of the breast.

Figure 2:
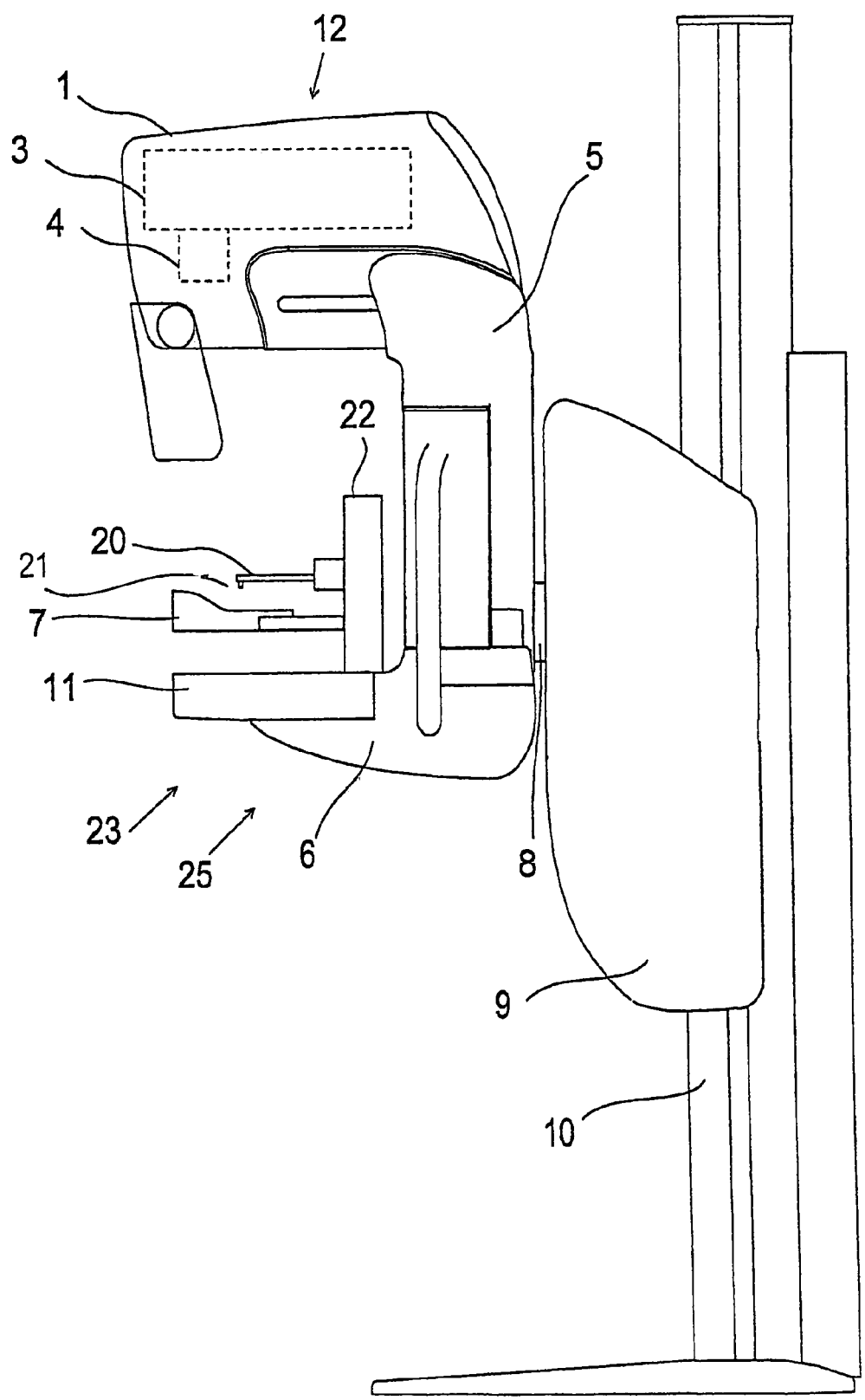
FIG. 2 shows schematically a biopsy arrangement of the invention in a mammography apparatus.

The inventive biopsy device arrangement in a mammography apparatus, an example of which is shown in FIG. 2, is used for performing biopsy as follows. A biopsy device 20 is integrable with a digital mammography apparatus in such a way that biopsy can be performed by using a full field detector which is the same as the one used also for screening test procedures, for example. In the context of this patent application, integrable refers to the fact that a biopsy device can be integrated as a permanent member of a mammography apparatus or that a biopsy device is integrable with and disengageable from a mammography apparatus as desired. Integration is effected in such a way that the volume space of a biopsy needle 21, i.e. in other words that of a biopsy procedure, can be adapted to function in a desired location within the imaging field of a full field detector. The volume space comprises an object subjected to examination or biopsy, which in mammography refers to a breast or part of a breast. The volume space of biopsy is for example 5 cm×5 cm regarding its cross-sectional area parallel to the detector surface. The volume space of biopsy can be displaced within the imaging field of a full field detector as necessary. Said biopsy in a volume space and the displacement of a volume space are performed by means of a needle guide unit 22. Electronics and software required for operating a needle guide unit are located in the needle guide unit and/or elsewhere in an X-ray imaging apparatus or in an element external of the X-ray imaging unit.

Thus, the question is about a digital mammography apparatus, which is provided with a full field detector FFDM (Full Field Digital mammography), such as for example CCD detectors (Charge Coupled Device) and TFT detectors (Thin Film Transistors).

In prior art imaging processes, which employ a digital full field detector, a full breast imaging is performed the same way as, for example, in screening tests. A suspicious part of the breast, detected from a full breast image, is subjected to biopsy. In an implementation of the invention, the volume space of biopsy is guided to a desired location with respect to the detector field of a full field detector. Consequently, biopsy imaging can be limited to the volume space of biopsy, i.e. over a small section of the maximal imaging area of a full field detector. A suspicious section of the breast is subjected to imaging at least from two different angles 32, 34. Such images are used as a basis for compiling three-dimensional information, which is compiled preferably in the form of xyz coordinate system information. The compiled three-dimensional information is used as a basis for guiding a biopsy needle to remove a test specimen from a suspicious part of the breast.

Since it is an essential endeavor in X-ray imaging that a patient be exposed to as little radiation as possible, a volume space exposed to radiation is generally the very volume space to be imaged as well. This can be implemented also by means of an embodiment, wherein a region under examination is exposed to radiation and image information is compiled by using, as a detector required in biopsy imaging, a desired element of a full field detector 11, which takes an image of the volume space of biopsy. However, said desired element of the full field detector 11 can be a detector area, which is larger than what is required by the detector-surface directed cross-sectional area of a volume space exposed to radiation. Imaging can be performed for example by using the entire detector area of a full field detector. From compiled image information is isolated the image information, which is essential in terms of an object to be examined.

Figure 3:
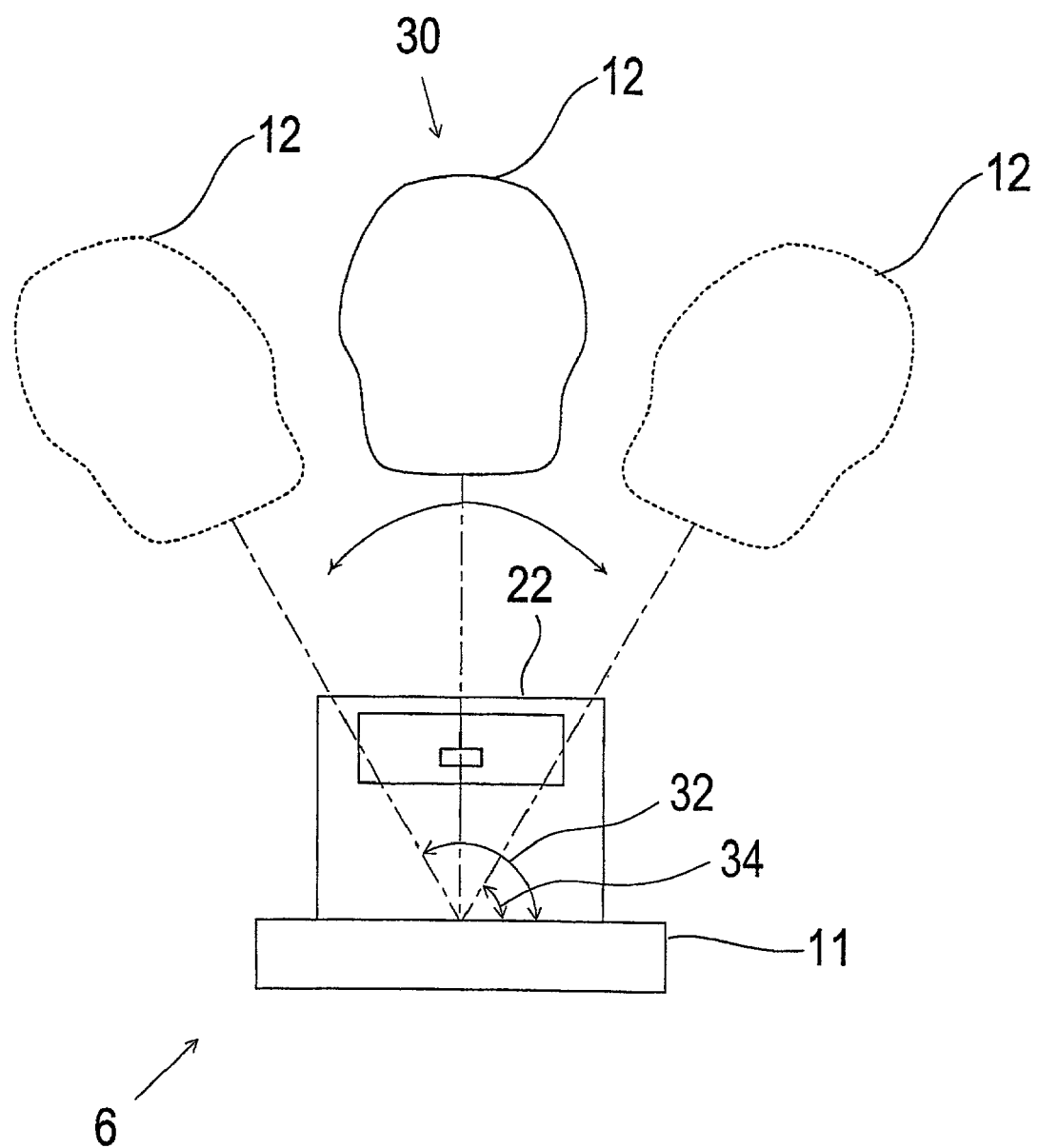
FIG. 3 illustrates stereotactic X-ray imaging.

FIG. 3 illustrates stereotacticity in mammographic X-ray imaging processes. A position 30 refers to the X-ray tube head 12 in a so-called basic position 30, wherein the X-ray tube head is at a substantially right angle relative to the full field detector 11. The X-ray tube head 12 can be maneuvered to at least two angles 32, 34 relative to the full field detector 11. Such angles can be for example 45 degrees and 135 degrees. As a result of the above, the mammography apparatus is capable of imaging a suspicious part of the breast from at least two different angles and compiling three-dimensional information on the basis of imaging procedures performed from said at least two different angles. A desired element of the full field detector 11 can be maneuvered within the field of the full field detector as a function of the angle formed by a volume space to be imaged and the full field detector. With regard to the X-ray imaging apparatus, FIG. 3 depicts elements which are sufficient to illustrate a displacement of the X-ray tube head to various angles 32, 34 relative to the full field detector 11 for stereotactic X-ray imaging. Otherwise, the question is about an X-ray imaging apparatus, such as shown for example in reference to FIGS. 1 and 2, respectively.

Three-dimensional information regarding the location of a suspicious part of the breast can also be compiled by applying TACT technology (Tuned Aperture Computed Tomography), which is described for example in publication U.S. Pat. No. 6,081,577 "Method and system for creating task-dependent three-dimensional images". In such technology, the basis is constituted by a reference point and X-ray images taken from various angles, for example from seven different angles, and this basis is used for creating three-dimensional X-ray information for example about a breast, which can be utilized for example in a biopsy procedure.

Figure 4:
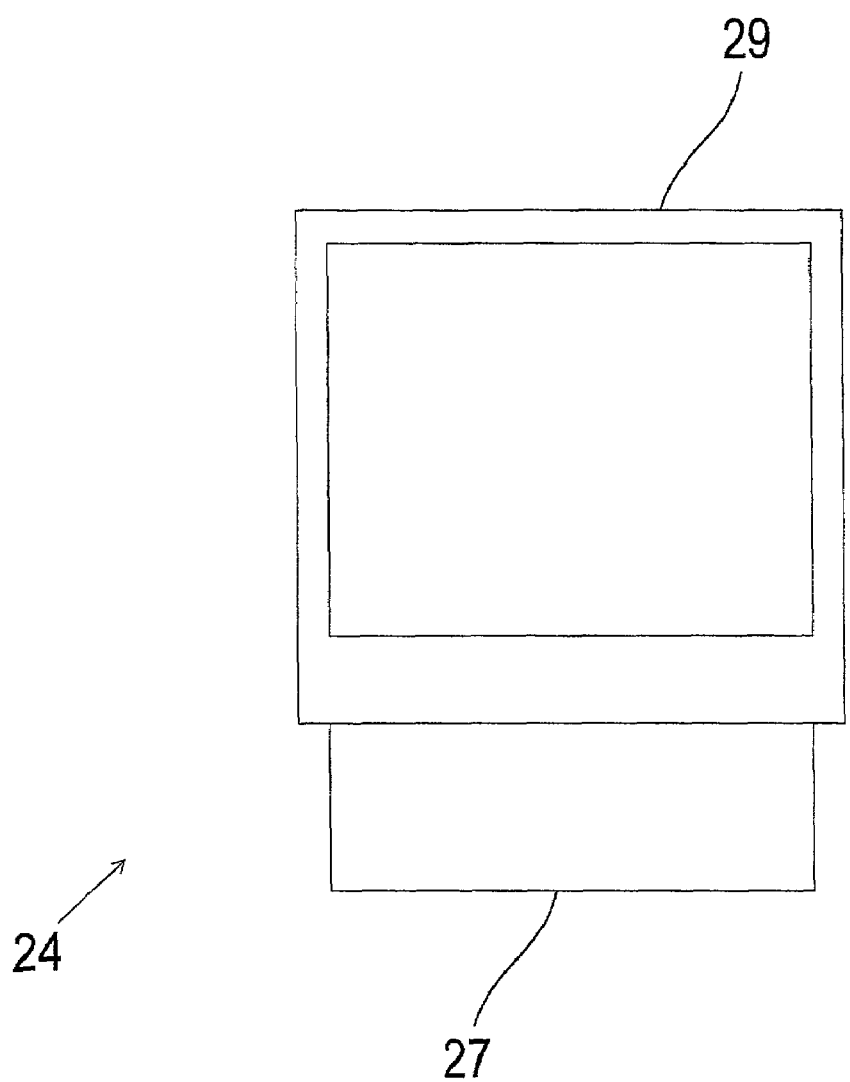
FIG. 4 depicts instruments for localizing an object from image information.

The above-described embodiments of the invention enable the exploitation of a method of the invention to be described next, and an arrangement for implementing the method, comprising a detector 11 for compiling or creating image information about an area or a volume space under review. The detector 11 can be any type of detector used for imaging, such as a full field detector 11 used for example in mammography. An object is localized from the compiled image information. Said localization is carried out with hardware 24 shown in FIG. 4, which are provided with a processor-based software configuration, such as for example a computer 27 and a display terminal 29 therefor. Preferably, the hardware or equipment 24 comprises a display terminal for reviewing image information, on the basis of which review an object is indicated from the image information for a closer examination. The region of radiation collimating an object is defined and imaging is performed by using for said imaging a section of the detector surface which images said collimated region of radiation. The collimation of irradiation is effected by means of a collimator 4. The arrangement comprises imaging equipment 25 for performing collimated imaging by using a section of the detector imaging field which images said collimated imaging field. The imaging equipment 25 is preferably provided with a processor-based software configuration for selecting a detector section required for imaging. In the context of this patent application, the arrangement for compiling image information refers to instruments necessary for image formation, which can be integrated or spaced apart within the imaging apparatus or separated therefrom. The area to be irradiated and imaged can be effectively defined in the above-described manner. This particular localizing irradiation and imaging of the invention can be exploited in all applications which involve irradiation and imaging of an object, like for example in a mammography apparatus during a biopsy procedure. The localizing irradiation and imaging of the invention can also be used during a breast examination phase, wherein the breast is compressed over a particular area for an enlarged image to be taken thereof. X-radiation is generated in the X-ray tube 3 and collimated in the collimator 4. Since the only area to be irradiated in X-ray imaging is a volume space to be imaged, the above-described inventive method is capable of minimizing the quantity of X-radiation received by a patient.

Technical implementations more detailed than the above have not been described, since those are technically, electronically and programmatically feasible with the use of prior art implementations.

Although the invention has been described above with reference to the accompanying drawings and specification, the invention is by no means limited to those and the invention is adaptable within the scope afforded by the appended claims.

The invention claimed is:

1. A mammography apparatus comprising:
a bracket (1, 5, 6) having first and second spaced bracket arms;
an X-ray tube head (12) fitted to said first bracket arm (1) and comprising an X-ray tube (3) for producing X-radiation and a collimator (4) for collimating the X-radiation produced by the X-ray tube;
compression means (7) for positioning a breast in the path of the collimated X-radiation of the X-ray tube head and for compressing the breast for imaging;
a biopsy device (20), integrable with said mammography apparatus proximate to said compression means, said biopsy device having a biopsy needle (21) for carrying out a biopsy in a localized volume space of biopsy within the breast;
an image forming component (23) fitted to said second bracket arm (6) to receive the X-radiation of said X-ray tube head passing through the breast, said image forming component comprising a digital full field detector (11) of a size that is sufficiently large to present a single image of the entire breast;
means for employing a small section of said full field detector as a detector element when the localized volume space of biopsy is imaged with collimated radiation from said X-ray tube head, said image forming component of said apparatus thus serving as an X-radiation detector for both full scale breast imaging and localized biopsy volume space imaging; and
a needle guiding unit (22) for guiding movement of the biopsy needle (21) in said localized volume space of biopsy on the basis of three-dimensional information compiled in the imaging of the localized volume space of biopsy.

2. A mammography apparatus as set forth in claim 1, wherein said X-ray tube head is movable to image the localized volume space of biopsy from at least two different angles for compiling three-dimensional information on the basis of imaging procedures performed from said at least two different angles.

3. A mammography apparatus as set forth in claim 1, wherein the X-ray tube head (12) is adapted to position itself at least at two different angles relative to the full field detector (11).

4. A mammography apparatus as set forth in claim 3, wherein the mammography apparatus comprises means to select said detector element of the full field detector (11) within the field of the full field detector as a function of an angle by which the volume space is imaged relative to the full field detector.

5. A mammography apparatus as set forth in claim 3, wherein the mammography apparatus comprises means to maneuver collimated X-radiation of the X-ray tube head within the field of the full field detector (11) as a function of an angle by which the volume space is imaged relative to the full field detector.

6. A method for performing biopsy of a breast, said method comprising the steps of:
- compressing the breast for retaining it for the duration of a biopsy procedure in an essentially static position in a mammography apparatus;
- placing a localized volume space of biopsy in the breast within an imaging field of a digital full field detector used for full scale breast imaging of the entire breast in a single image;
- generating collimated X-radiation from an X-ray tube head;
- exposing the localized volume space of biopsy with the collimated X-radiation;
- employing a small section of the digital full field detector as a detector element to receive collimated X-radiation passing through the localized volume space of biopsy;
- compiling three dimensional information from the received radiation; and
- guiding a biopsy needle (21) of a biopsy device to obtain a test specimen from a suspicious part of the breast in the volume space of biopsy on the basis of three-dimensional information compiled in the imaging of the localized space of biopsy.

7. A method as set forth in claim 6, wherein said method comprises imaging the localized volume space of biopsy from at least two different angles, said imaging procedures establishing a basis for compiling three-dimensional information.

8. A method as set forth in claim 7, wherein the detector element of the full field detector (11) is selected within the field of the full field detector as a function of an angle by which the volume space is imaged relative to the full field detector.

9. A method as set forth in claim 7, wherein the collimated X-radiation is maneuvered within the field of the full field detector (11) as a function of an angle by which the volume space is imaged relative to the full field detector.

* * * * *